United States Patent [19]
Logue et al.

[11] Patent Number: 5,700,571
[45] Date of Patent: Dec. 23, 1997

[54] RELEASE FILMS FORMED BY COEXTRUSION

[75] Inventors: Daniel R. Logue, Upland; Piet T. Van Emmerik, Claremont; Roger H. Mann, Corona del Mar; Edward I. Sun, Alhambra, all of Calif.; Gary A. Avalon, Painesville; Carol A. Caldwell, Kirtland Hills, both of Ohio; Eng-Pi Chang, Arcadia, Calif.; Richard A. Huskey, Mentor, Ohio

[73] Assignee: Avery Dennison Corporation, Pasadena, Calif.

[21] Appl. No.: 173,342

[22] Filed: Dec. 22, 1993

Related U.S. Application Data

[63] Continuation-in-part of Ser. No. 9,561, Jan. 25, 1993, abandoned.

[51] Int. Cl.$^6$ .............................. B32B 7/12; B32B 15/04; A61F 13/02
[52] U.S. Cl. .................. 428/352; 428/41.4; 428/41.8; 428/343; 428/354; 428/355
[58] Field of Search .................. 428/352, 40, 354, 428/355, 343, 41.4, 41.8

[56] References Cited

U.S. PATENT DOCUMENTS

| | | | |
|---|---|---|---|
| 2,532,011 | 11/1950 | Dahlquist et al. | 428/352 X |
| 3,262,327 | 7/1966 | Kallander et al. | 156/230 |
| 3,462,754 | 8/1969 | Bierenbaum et al. | 128/156 |
| 3,502,497 | 3/1970 | Crocker | 117/68.5 |
| 3,658,574 | 4/1972 | Izzi et al. | 428/352 X |
| 3,850,786 | 11/1974 | Jeffries et al. | 161/164 |
| 3,914,484 | 10/1975 | Creegan et al. | 428/42 |
| 3,963,851 | 6/1976 | Toyoda | 428/305 |
| 4,035,218 | 7/1977 | Yount | 156/289 |
| 4,177,812 | 12/1979 | Brown et al. | 128/284 |
| 4,189,419 | 2/1980 | Takemoto et al. | 260/29.7 |
| 4,339,485 | 7/1982 | Shibano et al. | 428/40 |
| 4,377,616 | 3/1983 | Ashcraft et al. | 428/213 |
| 4,379,806 | 4/1983 | Korpman | 428/354 |
| 4,398,985 | 8/1983 | Eagon | 156/233 |
| 4,451,610 | 5/1984 | Collister | 525/19 |
| 4,582,736 | 4/1986 | Duncan | 428/352 X |
| 4,626,460 | 12/1986 | Duncan | 428/352 X |
| 4,933,124 | 6/1990 | Duncan | 264/22 |
| 5,024,672 | 6/1991 | Widlund | 604/390 |
| 5,057,097 | 10/1991 | Gesp | 428/43 X |
| 5,106,383 | 4/1992 | Mulder et al. | 604/389 |
| 5,106,384 | 4/1992 | Polski | 604/390 |
| 5,124,187 | 6/1992 | Aeschbacher et al. | 428/40 |
| 5,183,705 | 2/1993 | Birkholz et al. | 428/343 |

*Primary Examiner*—Terrel Morris
*Attorney, Agent, or Firm*—Christie, Parker & Hale, LLP

[57] ABSTRACT

A release liner providing a release surface which comprises a first olefin polymer film formed having dispersed therein by high shear mixing a release substance which is polyethyleneimine octadecyl carbamide, polyvinyl octadecyl carbamate or a mixture thereof, coextruded or cocast onto a film formed from a second olefin polymer. The release liner has particular utility in diaper tape application.

9 Claims, 5 Drawing Sheets

RELEASE FILMS FORMED BY COEXTRUSION

This is a continuation in part of patent application Ser. No. 08/009,561 filed Jan. 25, 1993, now abandoned which is incorporated herein by reference.

FIELD OF THE INVENTION

The invention is directed to the use of long chained fatty acid carbamide and/or carbamate release additives to increase the release characteristics of coextruded olefin films.

BACKGROUND OF THE INVENTION

Polyvinyl octadecyl carbamate also known as polyvinyl stearyl carbamate has been applied as a coating from an organic solvent to paper substrates to serve as a release surface for pressure-sensitive adhesives.

Applications have ranged from self wound tapes to removable and repositionable note pad constructions.

U.S. Pat. Nos. 4,582,736 and 4,626,460 to Duncan, incorporated herein by reference, describe a biaxially oriented label stock comprising a laminate of a thermoplastic polymer matrix substrate layer having incorporated therein or applied thereto a coating of a pressure-sensitive adhesive layer and a release liner in the form of a polyolefin film having incorporated therein or applied to the surface thereof a release agent.

Included among the release agents disclosed is polyvinyl octadecyl carbamate. Activation of the release agent is realized through biaxially orientation of the film which causes the release material to come to the surface of the film.

U.S. Pat. No. 4,379,806 to Korpman discloses coextrusion of a pressure-sensitive adhesive layer and a backing film wherein the backing film or the adhesive layer contains a release agent and discloses, among other release agents, copolymers of stearyl methacrylate and acrylonitrile.

SUMMARY OF THE INVENTION

The present invention is directed to the use of a first olefin-based polymer film, preferably one based on polymerized ethylene, which contains a dispersed fatty acid carbamide and/or carbamate release material, and is coextruded or cocast with another olefin-based polymeric film, preferably a propylene-based polymeric film, to form a release film for pressure-sensitive adhesives. The films can be bound together directly or through a tie agent.

More particularly, the present invention is directed to the incorporation of a fatty acid carbamide and carbamate release additive into a first ethylene-based polymer under conditions of high shear. The first olefin polymer containing the release agent is coextruded with the second olefin-based film to form a release film for a pressure-sensitive adhesive.

The preferred systems are based on the incorporation of a polyethyleneimine octadecyl carbamide and/or a polyvinyl octadecyl carbamate, preferably polyvinyl octadecyl carbamate, into the first olefin polymer, preferably an ethylene-based, polymer which is cast or coextruded with a stiffening support film layer of a second olefin-based polymer preferably a propylene based polymer. The concentration of the release additive in the first olefin polymer film may range from about 0.1 to about 30 percent by weight, preferably from about 0.01 to about 15 percent, more preferably from about 0.3 to about 5 percent by weight for release tape application, most preferably from about 0.3 to about 0.6 percent. The preferred first olefin polymer is a low density polyethylene polymer. The preferred second olefin polymer is an isotactic propylene homopolymer and/or a random copolymer of propylene and ethylene which contains about 5 to about 10 percent by weight ethylene.

The coextruded products may be made by direct casting alone or with machine direction orientation.

The adhesives that may be applied are any solvent, hot-melt or emulsion pressure-sensitive adhesive, typically acrylic-based, rubber-based or silicone-based pressure-sensitive adhesives.

A particularly useful application for the products of the instant invention are as release films for use in diaper tape constructions such as fastening tapes, release tapes and target tapes.

DETAILED DESCRIPTION

The present invention is directed to self-supporting films formed by coextruding or cocasting a layer of a first olefin-based polymer containing polyethyleneimine octadecyl (stearyl) carbamide (PEOC) and/or polyvinyl octadecyl (stearyl) carbamate (PVOC) as a release agent onto a second olefin-based polymer support film.

By the term "first olefin-based polymer", there is meant polymers preferably based on ethylene such as herein low density ethylene homopolymers (PE), high density ethylene homopolymer (HDPE) elastomeric, ethylene-propylene copolymers (EPM) containing up to about 50% by weight propylene, blends of low or high density polyethylene with ethylene-propylene copolymers and/or polypropylene (PP), blends of ethylene-propylene copolymers with polypropylene and the like.

By the term "second olefin-based polymer", there is meant polymers based on propylene, preferably isotactic polypropylene and propylene-based copolymers containing minor amounts of other monomers including other olefin monomers containing two or four carbon atoms. The quantity of other monomers may be up to about 10 percent by weight of the total polymer, typically from about 5 to about 10 percent by weight of the total monomers. The presently preferred second olefin-based polymers are propylene homopolymers and random ethylene-propylene copolymers. Any product may include a tie component which may be a layer such as ethylene-vinyl acetate copolymer existing as a separate layer between the first and second olefin-based polymer films or as an additive to the second olefin-based polymer film. The films may also contain fillers, opacifiers and the like.

The presently preferred first olefin polymer film is a low density polyethylene known as 1017 manufactured and sold by Rexene.

The presently preferred release agent is polyvinyl octadecyl carbamate (PVOC).

The release agent incorporated into the first olefin-based polymer film may be in a concentration of from about 0.1 to about 30 percent by weight of the polymer and release agent, preferably from about 0.1 to about 15 percent by weight, or more preferably from 0.3 to 5% by weight based the a total weight of the polymer and release agent and more preferably form about 0.3 to about 0.6 percent by weight for diaper release tape applications.

It is presently preferred to dry blend the release additive material into the first olefin polymer film under conditions of high shear. This can be achieved by dry blending the particulate release additive into the olefin polymer by melt blending using a Sigma blade, Banbury mixer or the like. We have found that good blending cannot be achieved in a single screw extruder with any expectation of forming a coherent film due to the tendency of the release additive to remain as a discreet particulate solid. The required conditions of high shear cannot be achieved in a single screw extruder. The product thus formed can be transferred to a single screw extruder and coextruded with a polypropylene polymer film or recovered as pellets and subsequently added to an extruder.

In the combination, the first olefin-based polymer provides a relatively soft release surface for a pressure-sensitive adhesive while the second olefin polymer provides a stiff support or backing. The total thickness of the combination will range from about 0.5 to about 10 mils with the release agent containing first olefin polymer occupying from about 10 to about 50 percent of the total release liner thickness.

The release liner formed in accordance with this invention will function with any pressure-sensitive adhesive preferably acrylic and/or elastomeric (rubber) based silicone-based pressure-sensitives. The adhesives may be cast from solvent, emulsion or applied as a hot melt. The adhesive applied directly to the release liner after which there is added a backing or facestock or to the pressure-sensitive adhesive may be coated into the backing which is then laminated to the release liner. The release liner can serve as a self-wound tape where the adhesive is coated onto the second olefin polymer side and release provided by the first olefin polymer side.

The preferred acrylic pressure-sensitive adhesive polymers useful in accordance with the instant invention contain, on a percent by weight basis, from 30 to about 98 percent by weight of one or more alkyl acrylates containing from 4 to about 8 carbon atoms in the alkyl group. Preferably the total alkyl acrylate concentration is from about 60 to about 95 percent by weight based on the total weight of the monomers. Useful alkyl acrylates include n-butyl acrylate, 2-ethylhexyl acrylate, isooctyl acrylate and the like, with 2-ethylhexyl acrylate and mixtures of 2-ethylhexyl acrylate and butyl acrylate being preferred.

The second component of the acrylate polymers is one of more modifying monomers which affects the performance of the acrylate monomers. Among them there may be included one or more unsaturated carboxylic acids containing from 3 to about 5 carbon atoms normally present in an amount of about 2 to 10% by weight of the monomers forming the acrylic polymers. Unsaturated carboxylic acids included, among others, acrylic acid, methacrylic acid, itaconic acid and the like. Acrylic acid and methacrylic acid or mixtures thereof are presently preferred.

Other monomers which may be present are one or more vinyl esters which may be present in an amount of from about 15 to about 35 percent by weight of the total monomers and can include monomers such as vinyl acetate, vinyl butyrate, vinyl propanate, vinyl isobutyrate and the like.

In addition there may be provided one or more diesters of dicarboxylic acids, such as di-2-ethylhexyl maleate and di-2-ethylhexyl fumarate and the like.

The acrylic polymers are preferably prepared by emulsion polymerization in the presence of one or more surfactants including reactive surfactants which when reacted becomes part of the polymer. The acrylic polymer may be used as formed and, if desired, cross-linked either during or following polymerization by a conventional means and are provided as an emulsion having a solids content of 50 or more percent by weight solids , normally 60 or more percent by weight solids.

A presently preferred acrylic emulsion polymer is a cross-linked acrylic polymer containing butyl acrylate, 2-ethylhexyl acrylate and an unsaturated carboxylic acid sold as AE220CX by Avery Dennison Chemical Division of Avery Dennison Corporation.

Polymers used in formulating the rubber-based pressure-sensitive adhesives of this invention are based on natural and/or synthetic elastomeric polymers. Useful are AB, ABA and $(AB)_x$ block copolymers wherein x has a value of 3 or more and wherein A is a block comprising at least one monoalkenyl arene, preferably styrene, alpha methyl styrene, vinyl toluene and the like, and B is an elastomeric conjugated diene block, preferably a polybutadiene or a polyisoprene block.

Among the useful elastomeric polymers there may be mentioned natural rubber (polyisoprene), polybutadiene, synthetic polyisoprene, random styrene-butadiene copolymers, styrene-butadiene (SB) block copolymers, multi-armed $(SB)_x$ block copolymers, styrene-butadiene-styrene (SBS) block copolymers, styrene-isoprene (SI) block copolymers, styrene-isoprene-styrene (SIS) block copolymers, multi-armed styrene-isoprene $(SI)_x$ block copolymers, and the like.

Commercial elastomeric polymers used include linear SIS/SI block copolymers known as Kraton D-1107 and D-1112, SBS/SB block copolymers known as Kraton D-1101, D-1102 and DX-1300, and an $(SI)_x$ block copolymer known as Kraton D-1320X all manufactured and sold by Shell Chemical Company, and an SB block copolymer known as Solprene 1205 manufactured and sold by Housemex, Inc. In many of the SIS or SBS block copolymers, there are respectively present SI or SB components.

Other elastomers, such as the ethylene-propylene diene rubbers, styrene-ethylene/butylene-styrene block copolymers, styrene-ethylene/propylene-styrene block copolymers and the like, may also be used.

Preferably a mix is employed, the mix being based on a polybutadiene block copolymer and polyisoprene block copolymer.

When a mixture of butadiene-based and isoprene-based polymers are employed, the weight ratio of the polybutadiene containing constituents of the mixture to the polyisoprene constituents of the mixture are such that there are provided two peaks on the DMS curve for the mixture. Generally, weight ratios will range from about 0.5:1 upward. Compositions contemplated to be used in accordance with the instant invention are combined in ratio of about 0.5:1 to about 5:1, preferably from about 1:1 to about 1.5:1, and most preferably from about 1.3:1.

The rubbery copolymers preferably formed into a pressure-sensitive adhesive by addition of a "tackifier system" which consists of tackifiers include normally liquid and/or solid tackifiers which increase the glass transition temperature of the elastomeric block in which they are soluble. There may also be employed plasticizers and oils which lower glass transition temperature.

Tackifier systems used in the practice of the instant invention, include conventional tackifiers and plasticizers and oils, and for the preferred blends of incompatible elastomers have the net effect of being preferentially soluble in the polyisoprene block so as to preferentially increase the difference between the glass transition temperature of the polyisoprene block component relative to the polybutadiene block component, with an increase (amplification) of the tangent delta of the polyisoprene peaks of the pressure-sensitive adhesive composition.

Tackifier additives for the polyisoprene component are preferably obtained by the polymerization of a stream of aliphatic petroleum derivatives in the form of dienes and mono-olefins containing 5 or 6 carbon atoms generally in accordance with the teachings of U.S. Pat. Nos. 3,577,398 to Pace and 3,692,756 to St. Cyr, both incorporated herein by reference. The resultant hydrocarbons range from materials which are normally liquid at room temperature to those which are normally solid at room temperature and typically contain 40% or more by weight polymerized dienes. The dienes are typically piperylene and/or isoprene. They are sold by the Chemical Division of Goodyear Tire and Rubber Company as the Wingtack family of resins with the numerical designation being the softening point, e.g., Wingtack 95 which is normally a solid resin having a softening point of about 95° C. and Wingtack 10 which is normally a liquid resin having a softening point of about 10° C.

Other normally solid tackifiers are Escorez 1310 LC manufactured by Exxon and Piccotac 95 manufactured by Hercules.

Other additives which may serve a tackifier function include hydrogenated aromatic resins wherein a very substantial portion, if not all, of the benzene rings are converted to cyclohexane rings. They include the Regalrez family of resins manufactured by Hercules such as Regalrez 1018, 1033, 1065, 1078 and 1126, and Regalite R-100, and the Arkon family of resins from Arakwa Chemical such as Arkon P-85, P-100, P-115 and P-125), hydrogenated polycyclic resins (typically dicyclopentadiene resins such as Escorez 5300, 5320, 5340 and 5380 manufactured by Exxon) and the like.

There can also be added rosins, rosin esters, polyterpenes and other tackifiers which are compatible to some degree with the polyisoprene and polybutadiene phases. Other additives include plasticizer oils such as Shellflex 371 manufactured by Shell and Kaydol mineral oil manufactured by Witco which are soluble in both the polyisoprene and polybutadiene phases.

The tackifier system may be present in an amount, based on the total weight of tackifier system and elastomers, of from about 50% to about 80% by weight, preferably from about 50% to about 70% by weight, more preferably from about 60% to about 70% by weight. The presently preferred ratio is about 38% by weight elastomer and about 62% by weight tackifying resin additive, the resin additive preferably being a mixture of a normally solid tackifier such as Wingtack 95 or Escorez 1310 LC and a normally liquid tackifier such as Wingtack 10 or a plasticizer oil such as Shellflex 371. Polystyrene reinforcing additives may be present but are not required.

Figure 5:
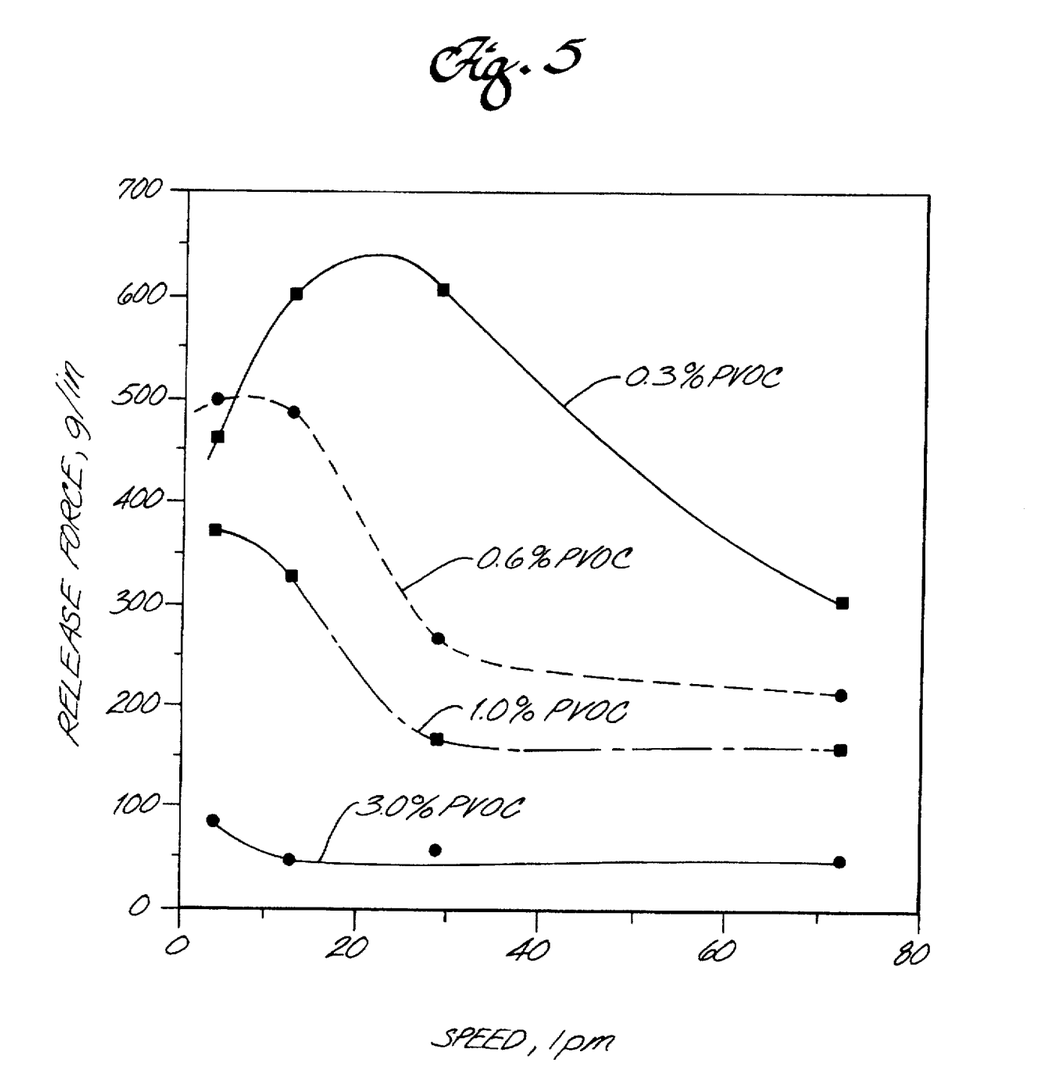
FIG. 5 is a plot of release force vs. speed of release for various concentrates of PVOC.

A particular utility for the products of invention are release tapes, fastening tapes, and target tapes used in diaper constructs such as those described in U.S. Pat. No. 5,057,097 to Gesp and U.S. Pat. No. 5,024,672 to Widlund, each incorporated herein by reference. Gesp shows in FIGS. 5 and 6 the cooperation with release and fastening tape in a diaper construction while Widlund shows the fastening tape used with a target tape. The target tape is bonded to shell of the diaper by any adhesive including pressure-sensitive and heat-activated adhesives enabling the use of thinner shells for the diaper construction.

In the following Examples and Controls "Ex" means Example, "Cont" means control. "TLMI" means Tape and Label Manufacturers Institute, The TLMI release is 90° peel test according to test procedure. The following adhesives were evaluated.

| Adhesive | Type | Source |
|---|---|---|
| 86-15 | Experimental Hot Metal Acrylic | Avery Dennison Chemical |
| I-679 | Solvent Acrylic | Avery Dennison Chemical |
| 239-50 | Experimental Emulsion Acrylic | Avery Dennison Chemical |
| AE220XC | Cross linked Emulsion Acrylic | Avery Dennison Chemical |
| AE2000 | Emulsion Acrylic | Avery Dennison Chemical |
| S-450 | Emulsion Rubber | Avery Dennison Chemical |
| AT-1, 220 | Emulsion Acrylic | Avery Dennison Chemical |
| P-904 | Silicone | Permacel |
| S-246 | Hot melt rubber based | Avery Dennison |
| CT-575 | Solvent Rubber based | Avery Dennison |

CONTROL 1 AND EXAMPLES 1-3

To test release properties of a low density polyethylene film containing polyethyleneimine octadecyl carbamide (PEOC) was a polyethyleneimine octadecyl carbamide incorporated into polyethylene 1017 in an extruder. The extruder had three zones; the first zone had a temperature of 150° C., the second zone had a temperature of 170° C. and the third zone had a temperature of 190° C. The extruder die temperature was 210° C. and the rate of extrusion was five feet per minute at a head pressure of 800 psi with the screw operating at 35 rpm. The addition of 10, 20 and 30% of the carbamide to the polyethylene provided a material which extruded but where the carbamide became tacky and caused sticking to the extruded screw and extruder die. The extruded films were cut into eight inch long strips and three-quarter inch 810 tape manufactured by 3M was applied and rolled down with a 4.5 pound roller. The samples were allowed to dwell for 20 minutes before testing. The tests were run on a TLMI release tester at a 90° peel angle at a peel rate of 300 inches per minute. Table 1 shows the average peel force required to separate the extruded films from the 810 tape. TLMI force in Newtons per meter (N/m) in an average of 3 samples as is film thickness in mils.

TABLE 1

| Cont/Ex | % Carbamide | Film Thickness | TLMI, N/M |
|---|---|---|---|
| Cont 1 | 0 | 7 | 113.3 |
| Ex 1 | 10 | 6.5 | 84.7 |
| Ex 2 | 20 | 4.5 | 66.7 |

TABLE 1-continued

| Cont/Ex | % Carbamide | Film Thickness | TLMI, N/M |
|---|---|---|---|
| Ex 3 | 30 | 2.5 | 90.0 |

CONTROL 2 AND EXAMPLES 4–7

Compositions containing 5, 10, 20 and 30% polyethyleneimine octadecyl carbamide (PEOC) and 20% polyvinyl octadecyl carbonate (PVOC) were formed using a two-zone Brabender mixer, each zone being at 160° C. All blends were mixed for 30 minutes and allowed to cool. The blended product was broken into small pieces using a polymer mill for subsequent addition to an extruder. The materials were extruded under the conditions shown in Table 2.

TABLE 2

| Cont/Ex | Zone 1, °C. | Zone 2, °C. | Zone 3, °C. | Head, °C. | Head Pressure | Screw RPM | % Release |
|---|---|---|---|---|---|---|---|
| Cont 2 | 150 | 170 | 190 | 210 | 740 | 15 | 0 |
| Ex 4 | 150 | 170 | 190 | 210 | 740 | 15 | 5 |
| Ex 5 | 150 | 200 | 220 | 225 | 610 | 13 | 10 |
| Ex 6 | 150 | 170 | 200 | 220 | 690 | 18 | 20 |
| Ex 7 | 150 | 170 | 200 | 220 | 690 | 20 | 5 |

Control 2 extruded with no problems. The film extruded with 5% PEOC had small particles in it. By raising the temperature and lowering the RPM's the number of particles was reduced. At 10% PEOC, even more particles were observed. An increase in extrusion temp. appeared to reduce particles. With 20% PEOC there was no observation of particles but the film that was extruded had small bubbles in it which caused small holes (fish eyes) in the film. By reduction of speed and temperature, the holes were eliminated but there were still bubbles in the film. The 30% PEOC was not extruded due to the problems with the 20% mix. For Example 7, 20% PVOC was substituted for PEOC. The blend extruded well and appeared to have no particles.

Table 3 shows TLMI release using 3M's 810 tape with a roll down pressure of 4.5 pounds. The results with various adhesives are shown in Table 4.

TABLE 3

| 90° Peel Testing of Extruded Release Systems ||||
|---|---|---|---|
| Cont/Ex | % Release Added | Film Thickness (mil) | TLMI 90° Release, N/M |
| Cont 2 | 0 | 5.0 | 74.75 |
| Ex 5 | 10% PEOC | 4–5 | 13.75 |
| Ex 4 | 5% PEOC | 3–4 | 50.5 |
| Ex 6 | 20% PEOC | 6.5–7 | Too Low to Read |
| Ex 7 | 20% PVOC | 5.5–6.0 | 17.75 |

TABLE 4

| Adhesive | PEOC % 5 Release, N/m | PEOC % 10 Release, N/m | PVOC % 20 Release, N/m |
|---|---|---|---|
| 1679 | 11 | 11 | 7.67 |
| AT-1 | 56 | 14.67 | 26 |
| S450 | 30.5 | 17.5 | 13.67 |
| 220HS | 60.5 | 20 | 38 |

TABLE 4-continued

| Adhesive | PEOC % 5 Release, N/m | PEOC % 10 Release, N/m | PVOC % 20 Release, N/m |
|---|---|---|---|
| S246 | 38.5 | 14.33 | 15.67 |
| CT575 | 83 | 29.3 | 41 |

CONTROL 3 AND EXAMPLES 8 AND 9

Figure 1:
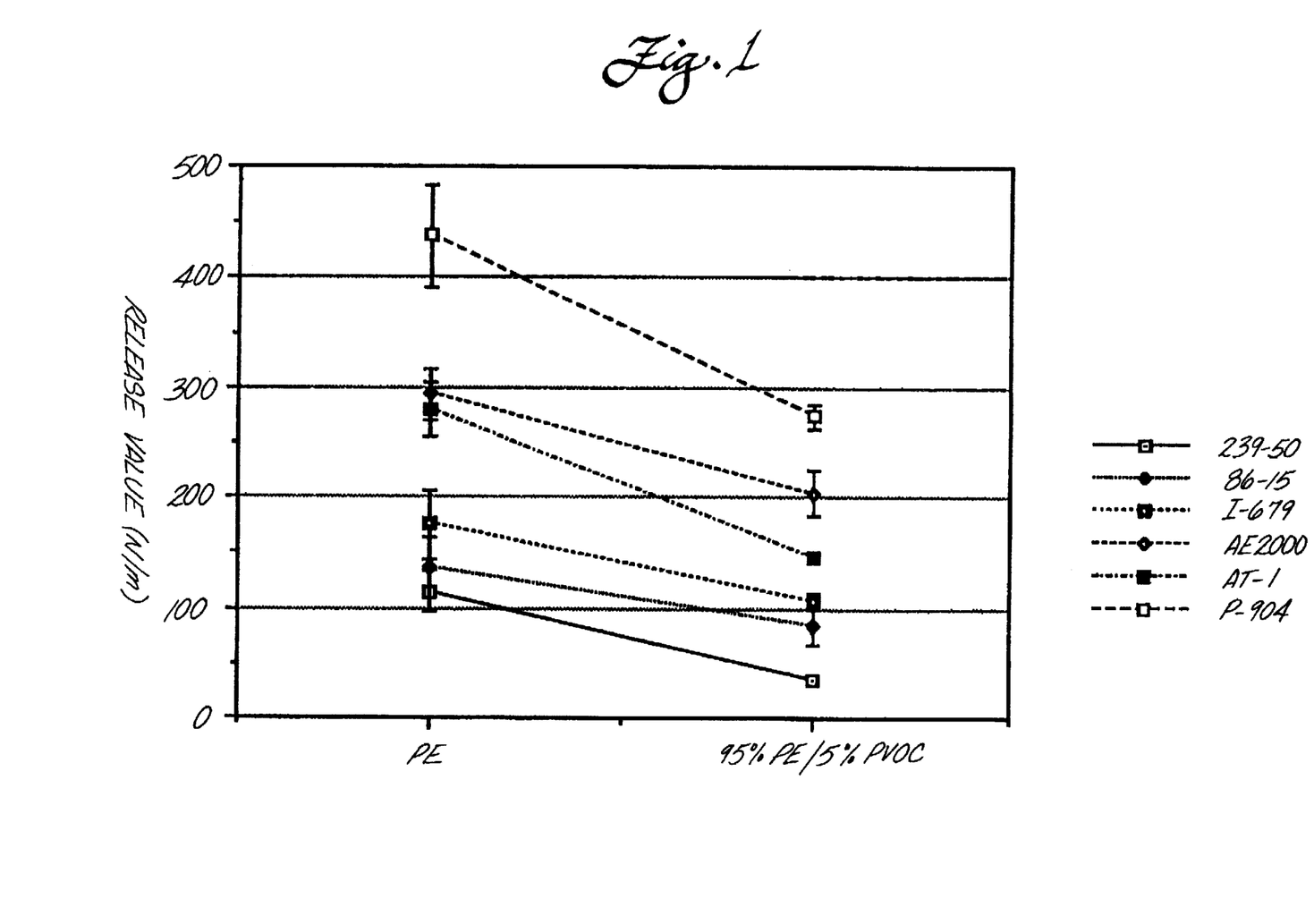
FIG. 1 is a graph illustrating the TLMI release value in Newtons per meter (N/m) from a variety of pressure-sensitive adhesives from low density polyethylene (PE) and polyethylene containing 5% by weight polyvinyl octadecyl carbamate (PVOC).

There was coextruded for Examples 8 and 9 a blend in part by weight of, 95 parts low density polyethylene 1017 and 5% parts PVOC. The backing is either a propylene homopolymer or a copolymer of ethylene and propylene. The release as compared to polyethylene alone from a substrate was determined for a variety of adhesives. The results are shown in Tables 5 and 6 and plotted in part on attached FIG. 1. In all instances, the release value in Newtons per meter was determined at a peel rate of 0.3 meter per minute. The addition of 5% PVOC significantly reduced the force required to peel the tape from the release surface or, in some instances, prevented transfer or welding.

TABLE 5

| Cont/Ex | Cont 3 | Ex 8 |
|---|---|---|
| Release layer | 100% PE[1] | 95% PE[1], 5% PVOC |
| Backing layer | Shell 5A97[2] | Shell 5A97[2] |
| Adhesives | Release N/m | Release N/m |
| 85-16 | 137[3] | 84[3] |
| 1-679 | 175[3] | 106.1[3] |
| 239-50 | 115[3] | 98 |
| AE220XC | Transfer[4] | 98 |
| AE2000 | 294[3] | 204 |
| S-450 | Weld[5] | 150[3] |
| AT-1 | 280 | 145 |

[1]Rexene 1017.
[2]Polypropylene homopolymer.
[3]Zippy release.
[4]Adhesive transferred to release liner.
[5]Adhesive weld to release liner.

TABLE 6

| Cont/Ex | Cont 3 | Ex 9 |
|---|---|---|
| Release layer | PE 1017[1] | 95% PE1017 5% PVOC |
| Backing Layer | PP 5A97[2] | Exxon PD 9263[3] |
| Release, Adhesive P-904 N/m | 437 | 274 |

[1]Rexene 1017.
[2]Polypropylene homopolymer.
[3]Random copolymer of propylene and ethylene.

CONTROLS 4 AND 5 AND EXAMPLES 10 AND 11

Figure 2:
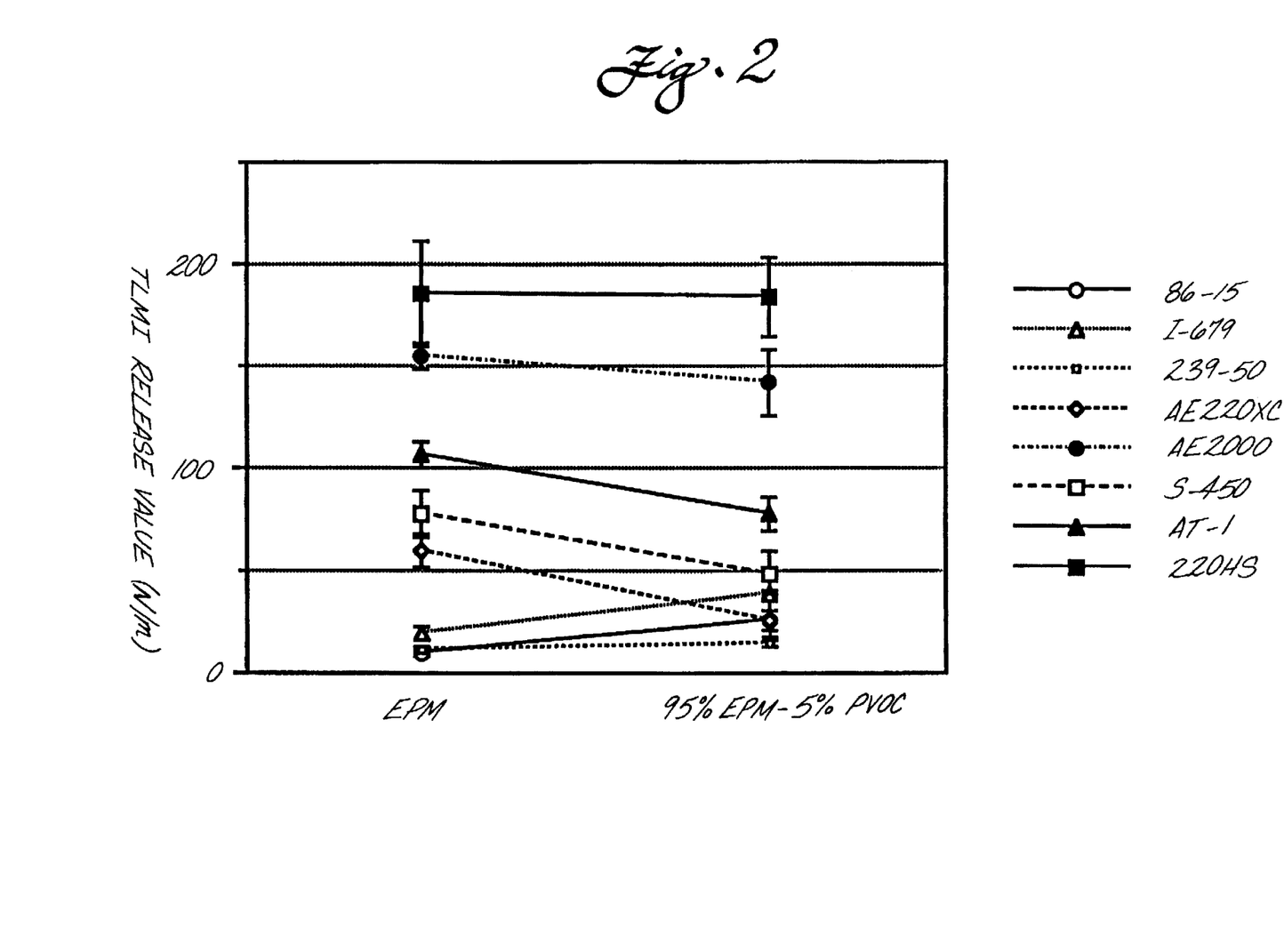
FIG. 2 is a graph which compares the release of various adhesives from EPM alone to EPM containing 5% PVOC.
Figure 3:
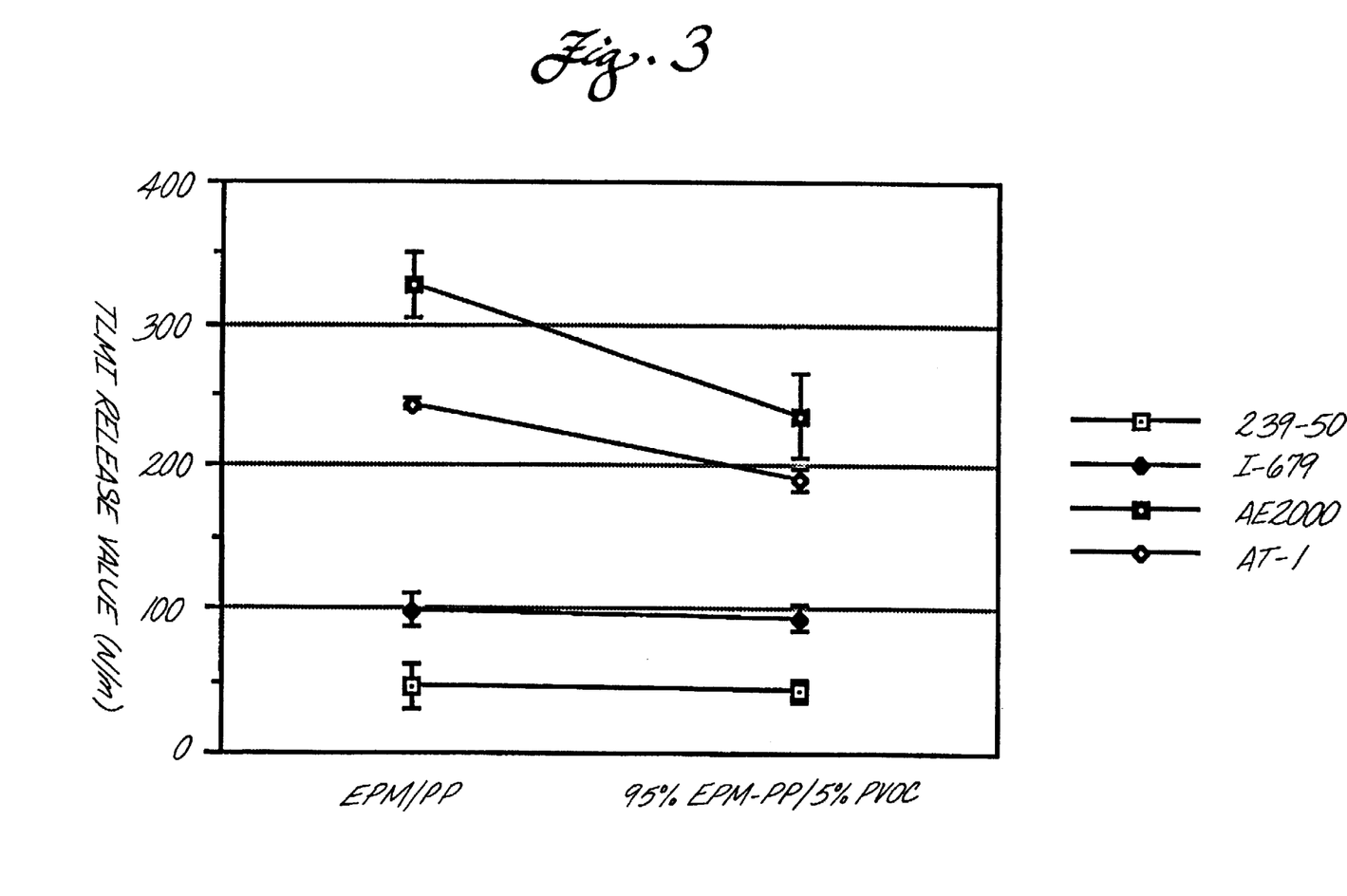
FIG. 3 is a chart that compares the release of a blend of ethylene propylene elastomer (EPM) and polypropylene (EPM/PP) and a mixture of 95 parts by weight of the same blend with 5 parts by weight PVOC.

There was compared the effect of a 5% additions of PVOC to an elastomeric ethylene-propylene copolymer EPM 306 (Ex. 4) and a blend thereof with a propylene homopolymer (Shell 5A9) (Ex. 11), with a propylene homopolymer backing to the corresponding construction not containing PVOC (Cont. 4 and 5). Some of the results are plotted in FIGS. 2 and 3.

TABLE 7

| Cont/EX | Cont 4 | Ex 10 |
| --- | --- | --- |
| Release layer | 100% EOM306[1] | 95% EPM306[1], 5% PVOC |
| Backing layer | Shell 5A97[2] | Shell 5A97[2] |
| Adhesives | Release, N/m | Release, N/m |
| 85-16 | 9.7 | 25.8 |
| 1-679 | 19.7 | 39.2 |
| 239-50 | 11 | 15.3 |
| AE220XC | 59 | 25.4 |
| AE2000 | 155 | 142 |
| S-450 | 78 | 49 |
| AT-1 | 106 | 77 |
| 220HS | 185 | 184 |

[1]Polysar EPM 306 random copolymer of ethylene and propylene.
[2]Shell 5A97 polypropylene homopolymer.

TABLE 8

| Cont/Ex | Cont 5 | Ex 11 |
| --- | --- | --- |
| Release layer | 50% EPM 306[1] 50% Shell 5A97[2] | 47.5% EPM[1], 47.5% Shell 5A97[2], 5% PVOC |
| Backing layer | Shell 5A97[2] | Shell 5A97[2] |
| Adhesives | Release, N/m | Release N/m |
| 239-50 | 47[3] | 43.8[3] |
| 1-679 | 99[3] | 94[3] |
| AE2000 | 327 | 236 |
| AT-1 | 243 | 191.5 |

[1]Random copolymer of ethylene and propylene.
[2]Polypropylene homopolymer.
[3]Zippy release.

Release Tape for Diaper Constructions

Conventional diaper tapes which have good adhesion performance, frequently rip the diaper shell when peeled at application speeds of about 300 in/min. Others which do not rip the shell frequently have low adhesion performance leading to pressure opening or "pop-open" during use. In order to provide a balance of good adhesion, without pop-open nor ripping of the shell, and simultaneously provide excellent refastenability, materials used for the fastening tape, the adhesive, the release coating and the backing are very important. In particular, the design of the landing zone and the tape are key to the total performance of the refastening diaper tape system.

There have been several types of release tapes in the market, such as silicone coated and polyvinyl octadecyl carbamate (PVOC) coated films or tapes. Such designs require sequential coating of the release onto a film or paper forming the tape. This is labor intensive and the coat weight and coverage of the coating have to be carefully controlled to achieve the desirable release levels.

By employing the tapes of this invention there is provided the advantage of fabricating the release film, in a one-step coextrusion process. In addition, the coextruded release film can be the outer shell of the diaper enclosure system without the need of a target landing zone.

Figure 4:
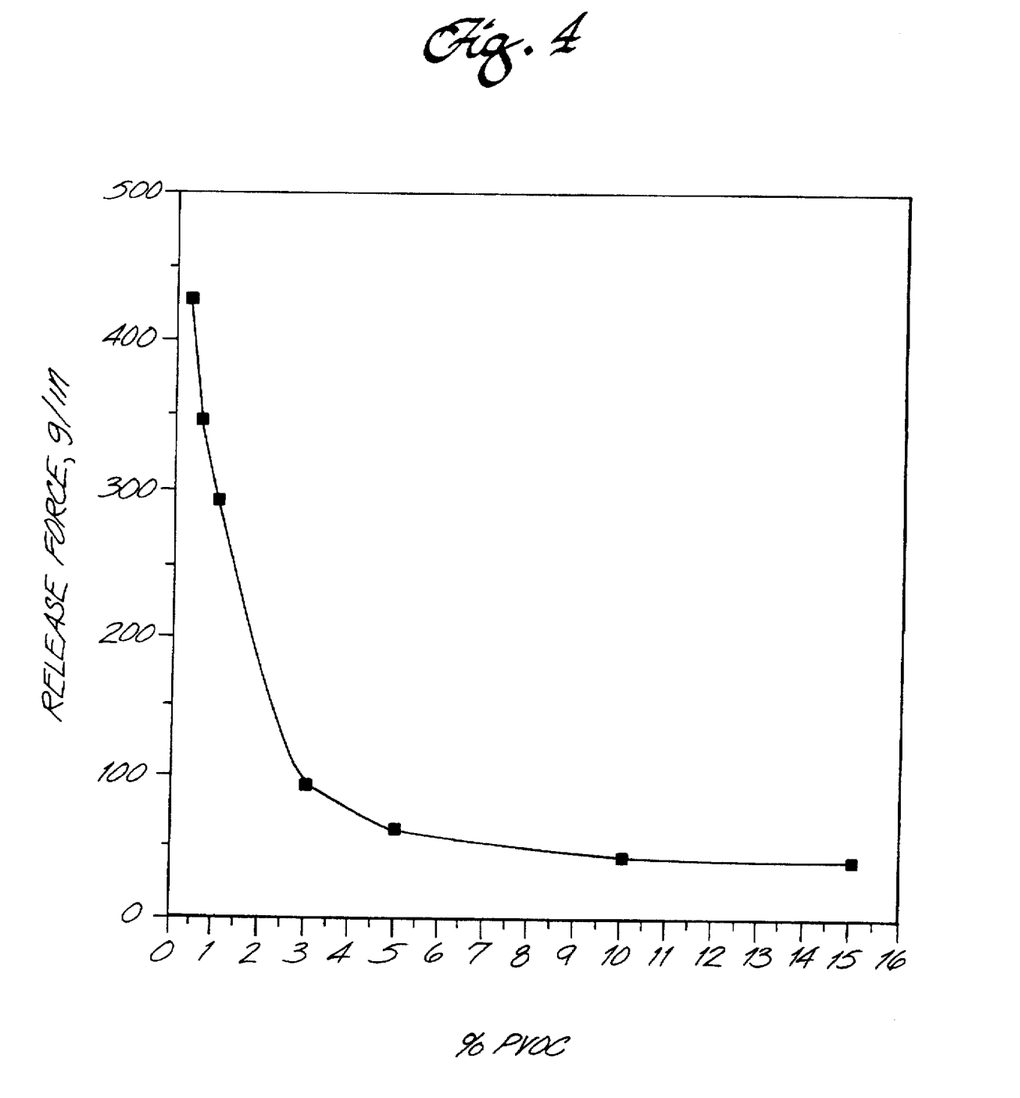
FIG. 4 shows the release force at 300 in/min of a diaper tape adhesive from polyvinyl octyl carbamate PVOC polyethylene PE/PE-PP as a function of PVOC content.

FIG. 4 shows the release force at 300 in/min, of a diaper tape adhesive, I-430 a tackified hot melt styrene isoprene-styrene, styrene isoprene adhesive, from PVOC/PE/PE-PP coextruded films with varying percentage content of PVOC. FIG. 4 establishes that as the PVOC percent increases, there is a drastic drop in release force, initially from 0.3 to 3% PVOC, after 5% PVOC the release force showed only a very gradual decrease in release force. The desirable release force for a diaper fastening system to prevent pop-open and ripping of the diaper shell is in the range of 300 to 500 g/in for unreinforced and 600 to 800 g/in for reinforced diapers. The data in FIG. 4 indicate that for such diaper tape release applications, the PVOC percent has to be lower than 1 percent.

Based on the above findings, coextruded films with PVOC concentrations at and 0.3% 0.6, and PVOC were tested with to determine their release forces and aging performance.

In order to test for migration, films were stored in an oven at 130° F. for 18 days in a simulated self-would form so that the back (nonrelease side) of film could be tested for transfer. Table 9 summarizes the results.

TABLE 9

Effect of Elevated Temperature Aging on Release Characteristics of FT-4912/4430 Test Tape from coextruded PVOC/PE/PP-PE at 12 in/min in a Simulated Self-Wound Film

| % PVOC | Temp, Deg. F. | PVOC Side g/in | Non PVOC Side g/in |
| --- | --- | --- | --- |
| 1 | 75 | 482 | 1310 (Polydeformation) |
| 0.6 | 75 | 630 | 1019 |
| 0.3 | 75 | 577 | 1316 (Polydeformation) |
| 1 | 130 | 462* | 978 |
| 0.6 | 130 | 591 | 1003 |
| 0.3 | 130 | 598 | 1072 |

POLYDEFORMATION = STRETCHING AND DEFORMATION OF THE FILM
*REPRESENTS ZIPPY PEEL AVERAGE (PEAK)

The data confirms that the release forces of coextruded films with 0.3 to 1% PVOC fall within the target window (300–800 g/in) of diaper applications. Besides the release force specification, another requirement is the effect of aging on release stability as well as absence of transfer of the coated PVOC onto the backside of a roll.

Heat aged results indicate that tapes containing 1% PVOC or below, PVOC did not appear migrate on the release (PVOC) side, in view of the insignificant change in values, but the nonrelease (back) side did experience differences which indicate possible migration. The 1% nonrelease side had the most pronounced drop from 1310 to 978 N/m a 34% change. The 0.3% and the 0.6% samples show a significantly lower or an insignificant drop. In view of the severity of the 18 days at 130° F. test treatment, the results for the 0.6% and 0.3% are rated as most promising concentrations for this invention.

To check the reproducibility of the results together with the speed dependence of the release characteristics, more testing was carried out using a different batch of samples. Table 10 shows the speed dependence of release for coextruded films with 0.3% to 3% PVOC with the test tape.

Table 10

Release Characteristics of FT-4912/4430 Test Tape from Coextruded PVOC/PE/PP-PE at Different Test Speeds in a Simulated Self-Wound Form

| Speed | % POVC | | | |
|---|---|---|---|---|
| | 0.3% | 0.6% | 1.0% | 3.0% |
| 4 ipm | 464(a) | 500 | 372 | 84(289) (b) |
| 12 ipm | 605 | 488(612) | 330(465) | 47(153) |
| 28 ipm | 606(680) | 270(590) | 167(386) | 59(125) |
| 72 ipm | 310(454) | 218(284) | 162(193) | 52(68) |

(a) IS AVERAGE PEEL G/IN.
(b) INDICATES ZIPPY PEEL WITH PEAK AVERAGE REPORTED

The 12 ipm results show good agreement with the results is reported in Table 9. For the coextruded films with 0.3% PVOC, the transition speed from a smooth to a zippy peel is about 28 ipm. As the concentration of PVOC increases, the transition speed drops to a lower speed, for example, (e.g., 0.6% and 1.0% PVOC coextruded films are both around 12 ipm, while at 3% PVOC release speed is below 4 ipm. In addition, the 0.6% films show a maximum release value at 4 ipm. This maximum appears to shift to lower PVOC concentration when the peel adhesion test was carried out at higher speeds. See FIG. 5. Again, based on the release force requirement and characteristics, coextruded films with 0.3% and 0.6% PVOC provide the best results.

What is claimed is:

1. A laminate release film providing a release surface which comprises a first film formed from a first olefin polymer selected from the group consisting of low density ethylene homopolymers, high density ethylene homopolymers, ethylene-propylene copolymers containing up to about 50% by weight propylene, blends of polyethylene with ethylene-propylene copolymers, polypropylene and mixtures thereof having uniformly dispersed therein by dry blending using high shear mixing a release agent selected from the group consisting of polyethyleneimine octadecyl carbamide, polyvinyl octadecyl carbamate and mixtures thereof present in an amount of from about 0.1 to about 20 percent by weight based on the weight of the first olefin polymer and release agent, said first film coextruded with or cocast onto and permanently bonded to a second olefin polymer fill, provided to stiffen the first olefin polymer fill, the second olefin polymer film selected from the group consisting of isotactic polypropylene and copolymers of propylene with at least one other olefin monomer containing 2 or 4 carbon atoms and in which the monomer is present in an amount up to about 10% by weight of the copolymer.

2. A laminate release film as claimed in claim 1 in which the olefin monomer is ethylene.

3. A laminate release film as claimed in claim 1 in which the first olefin polymer film is bonded to the second olefin film through a tie layer.

4. A laminate release film as claimed in claim 1 in which the release agent is present in an amount of from about 0.25 to about 15 percent by weight based on the weight of the release agent and first olefin polymer.

5. A laminate release film as claimed in claim 1 in which the release agent is present in an amount of from about 0.25 to about 5 percent by weight based on the weight of the release agent and first olefin polymer.

6. A laminate release film as claimed in claim 1 in which the release agent is present in an amount of from about 0.3 to about 5 percent by weight based on the weight of the release agent and the first olefin polymer.

7. A laminate release film as claimed in claim 1 in which the total thickness of the laminate is in the range of from 0.5 to about 10 mils and in which the release agent containing ethylene polymer occupies from about 10 to about 50% of the total laminate thickness.

8. A laminate release film as claimed in claim 1 combined with a layer of pressure-sensitive adhesive selected from the group consisting of acrylic-based pressure-sensitive adhesives, elastomeric rubber-based pressure-sensitive adhesives and a silicone adhesive, said layer of pressure-sensitive adhesive being applied to the second olefin polymer film.

9. A laminate release film as claimed in claim 8 in which the adhesive is applied in the form of a solvent, emulsion or a hot melt adhesive.

* * * * *